(12) United States Patent
Gemunder et al.

(10) Patent No.: US 6,485,301 B1
(45) Date of Patent: Nov. 26, 2002

(54) PHOTO-CURING LIGHT ASSEMBLY HAVING CALIBRATABLE LIGHT INTENSITY CONTROL

(75) Inventors: Elliot R. Gemunder, Dix Hills, NY (US); Hyeok-Jae (Daniel) Chi, Wheeling, IL (US)

(73) Assignee: Air Techniques, Inc., Hicksville, NY (US)

( * ) Notice: Subject to any disclaimer, the term of this patent is extended or adjusted under 35 U.S.C. 154(b) by 0 days.

(21) Appl. No.: 09/768,888

(22) Filed: Jan. 24, 2001

Related U.S. Application Data
(60) Provisional application No. 60/177,367, filed on Jan. 24, 2000.

(51) Int. Cl.[7] .................................................. A61C 3/00
(52) U.S. Cl. ........................................ 433/29; 250/205
(58) Field of Search ............................ 433/29, 27, 229; 250/205

(56) References Cited

U.S. PATENT DOCUMENTS

| | | | | |
|---|---|---|---|---|
| 6,008,264 A | * | 12/1999 | Ostler et al. | 522/4 |
| 6,103,203 A | * | 8/2000 | Fischer | 422/186 |
| 6,243,163 B1 | * | 6/2001 | Wakabayashi et al. | 356/326 |
| 6,309,216 B1 | * | 10/2001 | Parker | 433/29 |

* cited by examiner

Primary Examiner—John J. Wilson
Assistant Examiner—Melba Bumgarner
(74) Attorney, Agent, or Firm—Louis E. Marn; Clifford G. Frayne

(57) ABSTRACT

Applicant's invention relates to a photo-curing light assembly having calibration circuitry determinative of the intensity level of the light source and the generation of an analogue control voltage from a digital control voltage during use which automatically adjusts light intensity to achieve proper energy levels during programmed curing times.

9 Claims, 3 Drawing Sheets

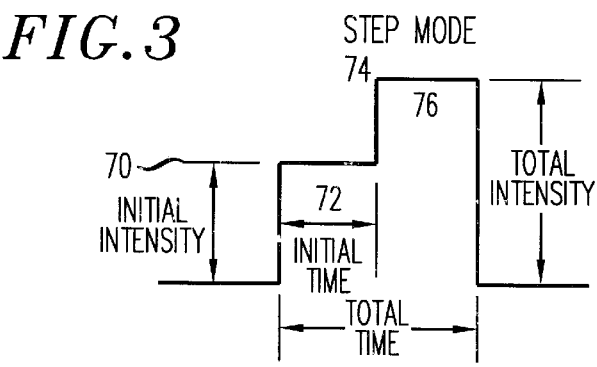
FIG.3 STEP MODE
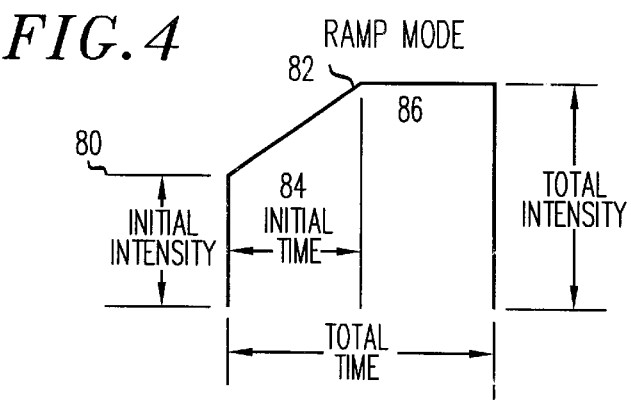
FIG.4 RAMP MODE
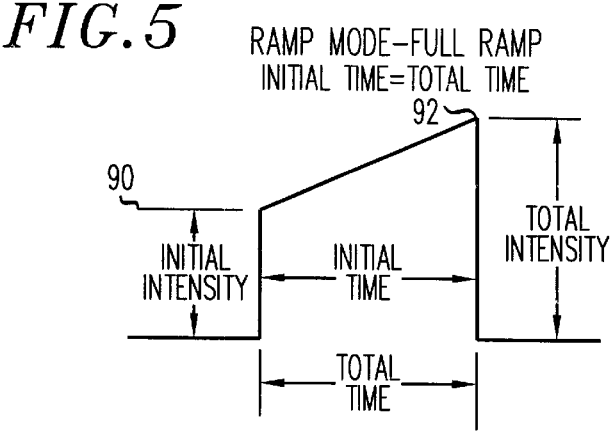
FIG.5 RAMP MODE-FULL RAMP
INITIAL TIME=TOTAL TIME
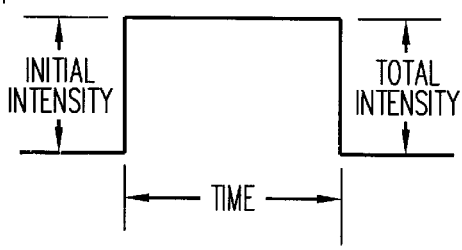
FIG.6
PRIOR ART

US 6,485,301 B1

PHOTO-CURING LIGHT ASSEMBLY HAVING CALIBRATABLE LIGHT INTENSITY CONTROL

RELATED APPLICATIONS

This application claims the benefit of provisional application 60/177,367 filed Jan. 24, 2000.

BACKGROUND OF THE INVENTION

1. Field of Invention

The present invention relates to a photo-curing light assembly for photosensitive compounds and more particularly to a photo-curing light assembly having calibration circuitry permitting lamp intensity control throughout time frame illumination.

2. Description of the Prior Art

Numerous substances are sensitive to light energy. One class of such substances undergo polymerization in response to applied light energy. Such class of substances includes composites and adhesives that have found uses in the dental arts for dental repair and the fabrication of dental prosthetics.

The time to cure a photosensitive composite or adhesive is a function of several factors, including the type of composite or adhesive, the amount of composite or adhesive required for the application, intensity of the light energy delivered, and the time duration of exposure. The intensity level of the light source decreases over the life of the source thereby affecting the intensity level and amount of light energy delivered to cure the composite or adhesive. In such situation, longer exposure times are required.

Adjustment of the exposure time includes the varying of the intensity of the light source, e.g. utilizing low intensity light over greater exposure times or high intensity light over shorter exposure times. Depending upon the type and amount of composite or adhesive being utilized, it may be beneficial to vary the intensity of the light during the actual photo-curing operation by either steadily increasing the intensity or stepping the intensity of the light over the exposure time. Pre-programmed photo-curing systems allow the user to select from two or more pre-programmed intensity modes. Since the intensity level of the curing lamp decreases over time there is a need to provide for a photo-curing assembly which provides for proper curing control notwithstanding any such diminished capacity of the curing lamp.

OBJECTS OF THE INVENTION

An object of the present invention is to provide for a novel photo-curing light assembly permitting the calibration of the intensity level of the light source prior to use.

A further object of the present invention is to provide a novel photo-curing light assembly permitting calibration of the intensity level of the light source in a fast and efficient manner.

A further object of the present invention is to provide for a novel photo-curing light assembly permitting calibration of the intensity level of the light source constantly permitting automatic readjustment of the light output during use to achieve proper curing energy level for the programmed curing time, not withstanding the diminished intensity of the curing lamp during its usable life.

A still further object of the present invention is to provide a novel photo-curing light assembly permitting the user to program a desired light intensity level over the duration time, to maintain a constant intensity, to increase intensity or to step intensity.

A still further object of the present invention is to provide a novel light curing assembly automatically increasing the duration time when the intensity level has reached its maximum output, but is unable to provide the required energy level for curing.

SUMMARY OF THE INVENTION

Applicant's invention relates to a photo-curing light assembly having calibration circuitry determinative of the intensity level of the light source and the generation of an analogue control voltage from a digital control voltage during use which automatically adjusts light intensity to achieve proper energy levels during programmed curing times.

BRIEF DESCRIPTION OF THE DRAWINGS

These and other objects of the present invention will become apparent particularly when considering the following detailed description and the accompanying drawings wherein:

FIGS. 3, 4, and 5 illustrate curing, wave shaping attainable by the photo-curing light system and the calibration method; and FIG. 6 illustrates the standard wave shape achieved by the prior art.

DETAILED DESCRIPTION OF THE INVENTION

Figure 1:
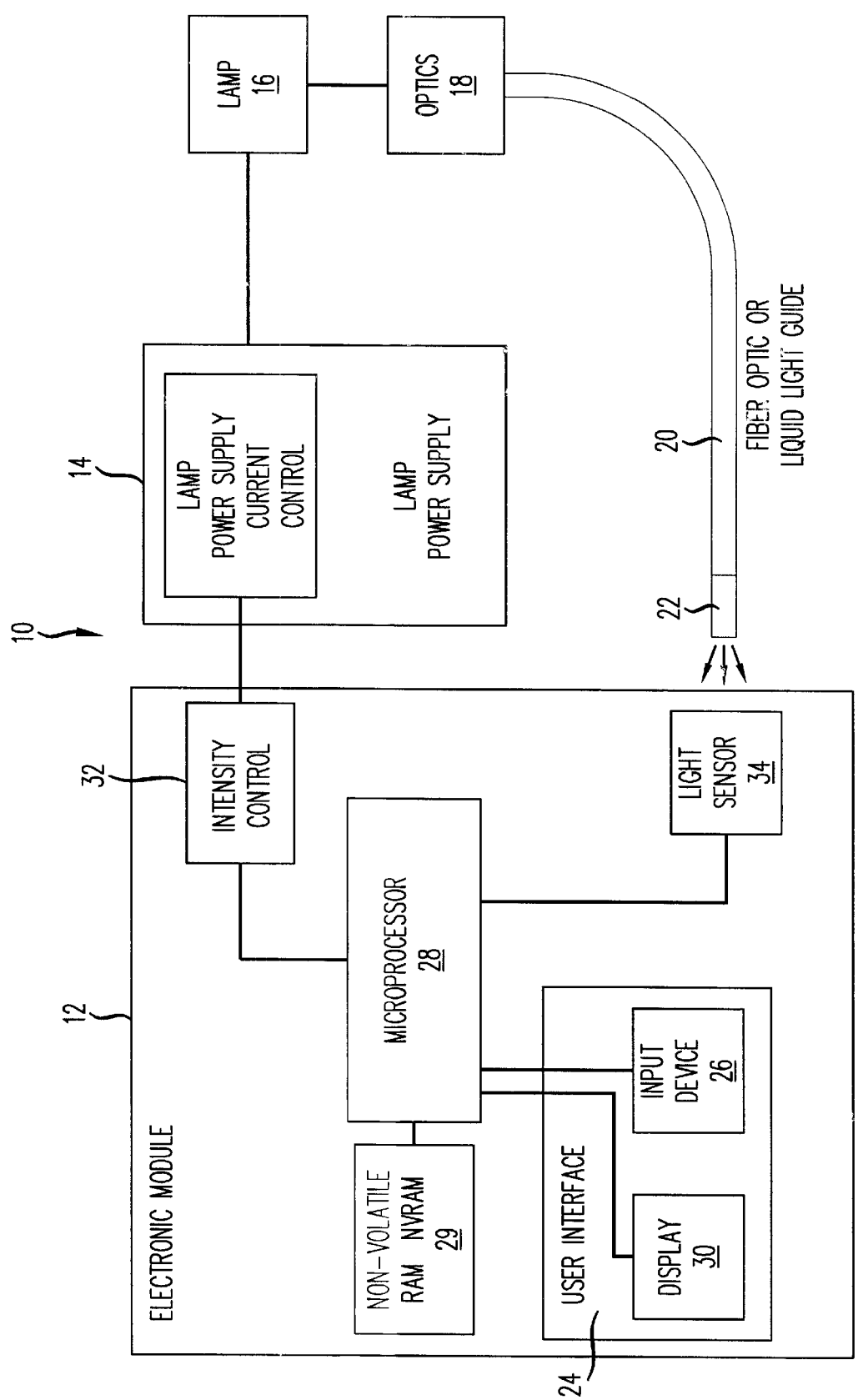
FIG. 1 is a block diagram of the photo-curing light system.

Referring now to the drawings, and particularly FIG. 1, there is provided a photo-curing light assembly of the present invention, generally indicated as 10, comprised of an electronic module 12, a curing lamp 16, power supply module 14, and an optics module 18. Such modules are mounted within a housing positioned proximate a dentist chair. Illumination from the lamp 16 is spectrally modified by the optic light guide 18 and transmitted to a tooth structure on which dental work is being performed. Transmission of such light is accomplished by a fiber optic or liquid core light guide 20 terminating in a curing tip 22 positioned in a dental hand piece (not shown).

The electronic module 12 of the photo-curing light assembly 10 is comprised of a microprocessor 28 provided with a nonvolatile RAM NVRAM 29, a user interface 24 comprised of an input pad device 26 and a display unit 30 and an intensity control 32. The microprocessor is connected to the input pad device 26 and display unit 30 of the user interface 24, to the intensity control unit 32 and the light sensor 34 within the electronic module 12. There is also included an amplifier 46 connected to a photodiode 44 having an external calibration post 40 provided with a diffuser glass 42. (See FIG. 2). In operation, the dentist or dental technician enters light intensity data and/or time duration data onto the input pad 26. Such data is communicated to the microprocessor 28(and displayed by the display device 30) and thence to the intensity control module 32 controlling curing lamp power supply 14 and the amount of current transmitting to curing lamp 16 to achieve the intensity selectively inputted via the input pad 26.

Over the course of time, the curing lamp 16 deteriorates in the amount of intensity which can be transmitted. Therefore, it is desirable to continuously know the maximum intensity of the curing lamp 16 at any time during use to adjust time duration needed to achieve proper curing. The light sensor 34 of the electronic module 12 senses light intensity emitted by the curing tip 22 to permit continuous calibration of the curing lamp 16, as herein more fully described.

Figure 2:
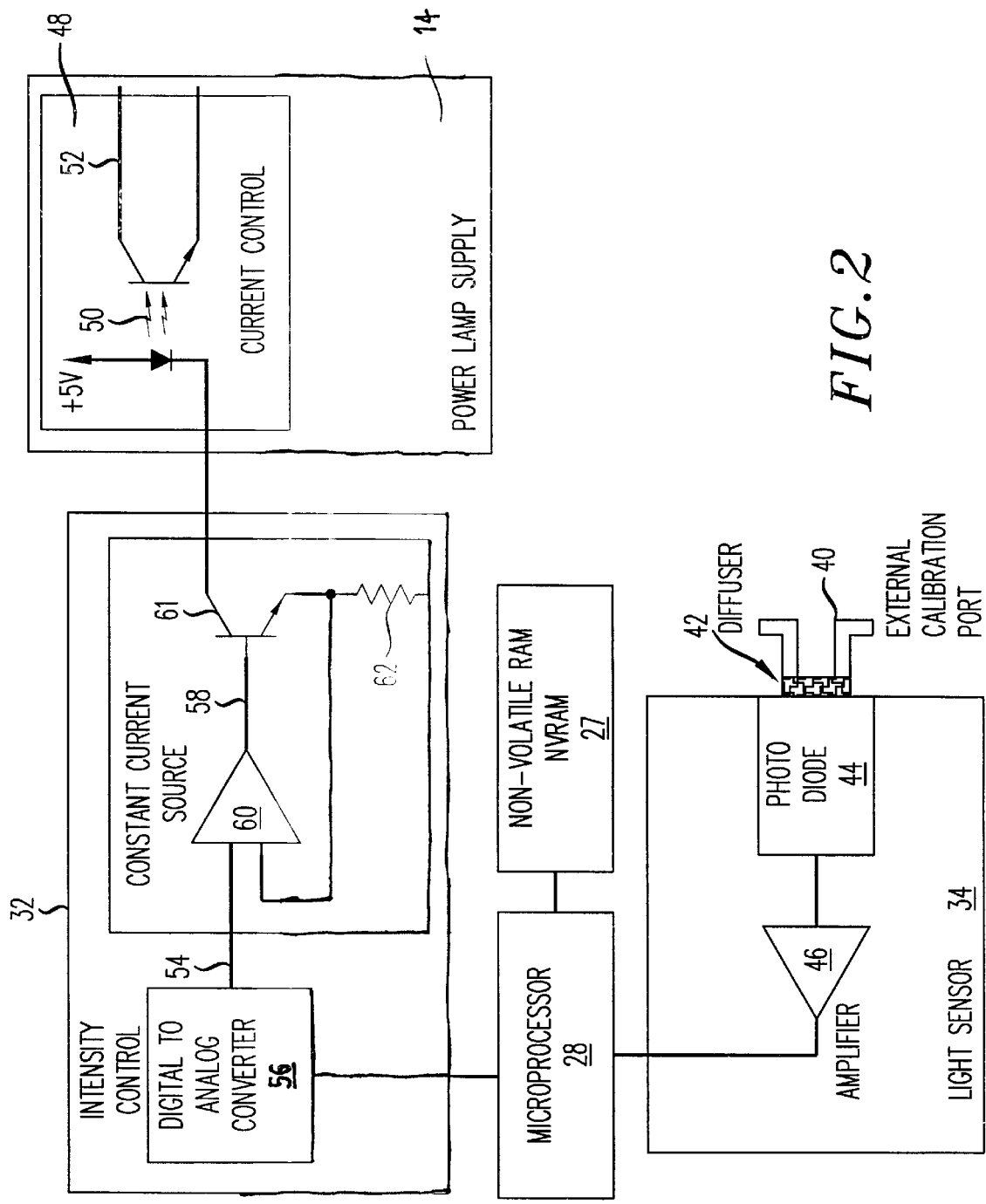
FIG. 2 is a detailed illustration of the calibration assembly.

The light sensor 34, referring to FIG. 2, includes an amplifier 46 connected to a photodiode 44 having an extended calibration port 40 provided with a diffuser glass 42. In operation, the curing tip 22 is inserted into the external radiometer calibration port 40 with light from the curing tip 22 illuminating the diffuser glass 42 to provide a uniform light beam. Such uniform light beam is viewed by the photodiode 44 having spectral response wave length is in the range of from 400 nm to 500 nm. The photodiode 44 in turn is in communication with the gain operational amplifier integrated circuit 46 generates a signal of the spectral response intensity from photodiode 44, and is thence transmitted to the microprocessor 28. Once the microprocessor 28 detects light, the calibration process is commenced.

Curing lamp 16 is caused to be automatically turned to its maximum light level and remain at such light level for a period of time to stabilize the light output. Such period of time is in the range of about 7 seconds. Once stabilized, the microprocessor 28 automatically reduces the light intensity of the curing lamp 16 to 50 percent of such maximum. Lamp current to the curing lamp 16 is adjusted until the signal level from the photodiode 44 circuit to the microprocessor 28 is nominally 50 percent. Such signal is stored in the nonvolatile RAM (NVRAM) integrated circuit 29. The microprocessor 28 then changes the control signal in five percent, increasing increments until 100 percent intensity is achieved. The signal level for each of these increments is stored in NVRAM 29.

Once 100 percent intensity is achieved, the process is reversed with the microprocessor 28 reducing the control signal by five percent increments from 100 percent to 50 percent. Each of these signals at the five percent increment levels is stored and replaces the stored signals of the ascending increments. The signals now stored in the NVRAM 29 are utilized in controlling the light intensity level during actual use. It is understood by one of ordinary skill in the art that calibration of the light output of the curing lamp is effected on a daily basis during the life of the curing lamp.

The entire calibration process takes approximately 10 seconds. At conclusion, the light output goes to the programmed level in the selected mode of operation as inputted by the user via the input pad 26. It can therefore be understood that the speed and accuracy of this calibration permits the dentist or dental technician to calibrate the instrument before each and every patient use, thereby assuring a more accurate cure and also permitting a greater variety of selected modes of cure.

The calibration method and scheme as described herein, assures the dentist and the dental technician that light intensity and duration are sufficient for the curing process being programmed. It allows the user to get the maximum life and benefit from the curing lamp 16 without premature replacement and serves as a warning to the user when lamp light guide or curing tip may have reached its life expectancy.

In operation, when light output from the curing tip 22 decreases, as measured by the external radiometer calibration port 40, the microprocessor controlled electronics automatically adjusts the light output to achieve proper curing energy or intensity for the programmed curing time as inputted on the input pad 26. When light output has been increased to its maximum output (and cannot produce the required curing energy for the programmed time), curing time is automatically increased by the microprocessor and is displayed in second increments. The maximum increase time which the microprocessor is automatically programmed is twice the program time inputted by user on the input pad 26. At such time, the display unit will flash indicating that the light output is reduced to one half of the maximum achievable output and the user can take appropriate action with respect to the curing lamp 16, light guide or curing tip.

Similarly, when the light output has been increased to its maximum output and the time has automatically increased to produce the proper curing energy, reducing the programmed intensity will automatically shorten the duration time.

Once the curing lamp 16 has been calibrated using the calibration method as set forth above, the light output can be controlled via settings selected in the programming mode by the dentist or dentist technician. The microprocessor 28 will automatically generate the proper signal levels based on the stored memory and the programmed inputs to control the lamp current such that the light output is set at the desired level which is a percentage of the maximum light output as defined by factory setting. The ability of the calibration method of the present invention to control the lamp current and hence lamp intensity is provided by an analog control voltage to the control line input of the high voltage power supply.

As illustrated in FIG. 2, an analog lamp control voltage signal 50 is digitally generated by microprocessor 28, and applied to the lamp current control line 52 controlling lamp intensity. Such analog control voltage 50 is digitally generated by the microprocessor 28 and converted to an analog signal 54 by means of a digital to analog converter circuit 56 which in turn is connected to a constant current circuit 58 utilizing an operational amplifier integrated circuit 60 and transistor 62. Thus, the microprocessor 28 utilizes the stored signal levels generated during the calibration process to generate the lamp current control signal 52 so as to generate a constant current to the lamp power supply 14 and thence to lamp 16. The microprocessor as a result of the calibration method will automatically adjust the time duration based upon the intensity of light available as a result of the age or use of the curing lamp 16 and condition of the light guide and curing tip.

The ability to calibrate the curing lamp 16 to ascertain its maximum intensity during life time allows the dentist or dentist technician the ability to accurately control light intensity and/or time duration in the programming of inputs to the microprocessor which permits accurate light output wave shaping.

FIG. 3 is illustrative of a step mode curing. Duration time is measured on the horizontal axis and light intensity measured on the vertical axis. The input pad 26 of the photo-curing light system 10 assembly permits the user to input multiple intensity and time levels resulting in a step mode curing wave shape where curing is initiated at an initial intensity 70 for an initial duration 72 and then increased to a second intensity 74 for a second duration 76.

FIG. 4 illustrates a partial ramp mode in which curing is begun at an initial intensity 80 and continually increased to a second intensity 82 over a time duration 84 and it is maintained at such second intensity 82 for a time duration 86.

FIG. 5 illustrates a full ramp mode with respect to the photo-curing light assembly 10 in which curing commences at an initial intensity 90 and continuously increases to a maximum intensity 92 over a time duration 94.

The wave shaping capabilities available to the user at the discretion of the user thereby permits the user to compensate for different types of photo-curable composites, adhesives, sealants, etc., and different thicknesses of photo-curable composites as applied to the tooth structure. The calibration scheme heretofore discussed provides the user with confidence that the desired intensity and desired time duration will be accurately provided by the photo-curing light system in order to insure adequate and total curing of the composite, adhesive or sealant.

If the light intensity of the curing lamp has been increased to its maximum and cannot produce the required curing energy, the programmed time is automatically increased to achieve the desired curing and the user can program the photo-curing light assembly to include curing at a fixed intensity, a continuously increasing intensity from one level of light output intensity to another level of light output intensity or in a step mode having a fixed level of initial light intensity for a fixed duration and an increase to a second level of fixed light intensity for a second fixed duration.

While the invention has been described in connection with an exemplary embodiment thereof, it will be understood that many modifications will be apparent to those of ordinary skill in the art; and that this application is intended to cover any adaptations or variations thereof. Therefore, it is manifestly intended that this invention be only limited by the claims and the equivalents thereof.

What is claimed:

1. A photocuring light assembly having calibration circuitry which comprises:

a curing lamp;

an optical light guide for providing light energy from said curing lamp;

a control unit generating digital control voltage converted to analogue control voltage for providing constant current to said curing lamp;

means for inputting irradiation data for curing a photo-sensitive composition;

means for displaying said irradiation data;

means for controlling light energy output to said control unit, said means for controlling light energy output including means for measuring light energy output from said optical light guide, said means for controlling light energy output programmed to incrementally increase light energy output to said curing lamp to a maximum light output while concomitantly recording and storing light energy levels, said means for controlling light energy output programmed to incrementally decrease light energy output from said maximum light output while concomitantly recording and storing light energy levels, whereby recorded and stored levels constitute light energy levels for subsequent use of said photocuring light assembly for photocuring a photo-sensitive composition.

2. The photo curing light assembly as defined in claim 1 wherein incremental increase in light energy output levels begin at about a level of 50% of said maximum light output with incremental increases at increments of 5% to said maximum light output.

3. The photocuring light assembly as defined in claim 2 wherein incremental decrease in light energy levels begin at said maximum light output with increments of 5% to said 50% of said maximum light output.

4. The photocuring light assembly as defined in claim 1 or 3 wherein said means for measuring light energy output from said optical light guide includes a photodiode having a diffuser glass to provide a uniform light beam.

5. The photocuring light assembly as defined in claim 1 or 3 wherein said means for controlling light energy output is activated upon reaching said maximum light output to said curing lamp and thereby initiates programming thereof to provide said recorded and stored levels.

6. The photocuring light assembly as defined in claim 1 or 3 wherein said means for controlling light energy output adjusts said means for inputting irradiation data to compensate for decrease in intensity of said curing lamp during useful life to achieve curing of said photosensitive composition.

7. The photocuring light assembly as defined in claim 1 or 3 wherein said means for controlling light energy output includes a program to provide different light output levels of said curing lamp during photocuring of said photosensitive composition.

8. The photocuring light assembly as defined in claim 7 wherein said program provides incremental increase in said light output levels of said curing lamp during photocuring of said photosensitive composition.

9. The photocuring light assembly as defined in claim 7 wherein said program provides incremental decrease in said light output levels of said curing lamp during photocuring of said photosensitive composition.

* * * * *